US00PP15621P2

(12) United States Plant Patent
Olesen et al.

(10) Patent No.: US PP15,621 P2
(45) Date of Patent: Mar. 1, 2005

(54) MINIATURE ROSE PLANT NAMED 'POULHI017'

(50) Latin Name: *Rosa hybrida*
Varietal Denomination: POULhi017

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/742,417

(22) Filed: Dec. 22, 2003

(51) Int. Cl.[7] ..... A01H 5/00
(52) U.S. Cl. ..... Plt./121
(58) Field of Search ..... Plt./121

*Primary Examiner*—Anne Marie Grunberg
*Assistant Examiner*—Annette H Para

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULhi017'.

SUMMARY OF THE INVENTION

The present discovery constitutes a new and distinct variety of a miniature pot rose plant which was discovered in a cultivated area. The mutation resulted from 'POULhi008', a miniature pot rose hybridized by the same inventors. The resulting mutation was selected and evaluations were conducted on the resulting rose plants in a controlled environment. 'POULhi008' is described and illustrated in U.S. Plant patent application Ser. No. 10/267,939 dated Oct. 8, 2002. The new rose variety resulted from a naturally occurring mutation of unknown causation on a branch of 'POULhi008'.

The rose plant of the present discovery has the following unique combination of characteristics which are outstanding in the new variety and which distinguish it from the original rose 'POULhi008'.

1. While the upper surface of flower petals on an open flower are Red Group 55 C and D on 'POULhi008', the same characteristic for 'POULhi017' is Red Group 55B.
2. 'POULhi017' has a longer lasting quality than 'POULhi008', which makes the variety more suitable for the floral industry.
3. Basal petal spots on flower petals of 'POULhi008' are Yellow Group 1A on both the upper and lower surfaces. Petals spots on flower petals of 'POULhi017' are Yellow Group 4D on the lower surface, and Yellow Group 4C on the upper surface.

The rose plant of the present discovery has a unique combination of characteristics which are outstanding in the new variety and which distinguish it from the original rose 'POULhi008' as well as all other varieties which we are aware of. For example, the new variety has:

1. Uniform and abundant pink flowers;
2. Vigorous and compact growth;
3. Year-round flowering under glasshouse conditions;

4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULhi017' from all other varieties of which we are aware.

Asexual reproduction of 'POULhi017' by cuttings and traditional budding was first done by L. Pernille and Mogens N. Olesen in their nursery in Fredensborg, Denmark in 1998. This initial and other subsequent propagations conducted in controlled environments have demonstrated that the characteristics of 'POULhi017' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'POULhi017'. Specifically illustrated in the drawing:

FIG. 1.1; Open flower, stem showing the attachment of leaves and peduncles;

FIG. 1.2; Flower bud closed, partially open, and open;

FIG. 1.3; Sepals, receptacle, and pedicel;

FIG. 1.4; Flower petals, detached;

FIG. 1.5; Mature leaf, upper and lower surface, and juvenile leaves;

FIG. 1.6; Bare stem.

DETAILED DESCRIPTION OF THE VARIETY

The following is a description of 'POULhi017', as observed in its growth in glasshouses in Fredensborg, Denmark. Observed plants were grown for a period of 3 months, in 15 cm pots. Color references are made using The Royal Horticultural Society (London, England) Colour Chart, 1995, except where common terms of color are used.

For a comparison, several physical characteristics of the rose variety 'POULarbso', a rose variety from the same inventors described and illustrated in U.S. Plant patent application Ser. No. 10/136,452 dated Apr. 29, 2002 are compared to 'POULhi017' in Chart 1.

CHART 1

| | 'POULhi017' | 'POULarbso' |
|---|---|---|
| Flower diameter when open. | 30 mm. | 45 mm to 55 mm. |
| Bud Color at ¼ Open. | Red Group 55B. | Red Group 52C. |
| Color of Upper Surface of Flower Petal On Open Flower. | Red Group 55B. | Red Group 48C. |

FLOWER AND FLOWER BUD

Blooming habit: Continuous.

Flower bud:

*Size.*—Upon opening, 26 mm in length from base of receptacle to end of bud. 12 mm in diameter.

*Bud form.*—Pointed ovoid.

*Bud color.*—As sepals unfold, Red Group 36B. Intonations of Red Group 55C. Red Group 55B at ¼ opening.

*Sepals.*—Upper Surface: Texture: Moderately pubescent. Color: Green Group 147B. Lower Surface: Color: Yellow-Green Group 144A to Green Group 143B. Shape: Sepal apex is cirrose. Base is flat at union with receptacle. Margins: Margins have strong foliaceous appendages on three of the five sepals. Size: 37 mm (l)×10 mm (w).

*Receptacle.*—Surface: Smooth. Shape: Urn-shaped. Size: 6 mm (h)×9 mm (w). Color: Yellow-Green Group 144A.

*Peduncle.*—Surface: Medium amount of stipitate glands. Length: 20 to 30 mm. Color: Yellow-Green Group 144A. Strength: Strong.

*Borne.*—In small clusters. 1 to 3 flower buds per stem on average.

Flower bloom:

*Fragrance.*—Moderate rose scent.

*Duration.*—The blooms have a duration on the plant of approximately 10 to 14 days. Afterwards, petals fall cleanly away from plant.

*Size.*—Average flower diameter is 30 mm when open.

*Form.*—Open cup.

*Shape of flower when viewed from the side.*—Upon opening, upper part: Flat. Upon opening, lower part: Concave. Open flower, upper part: Flattened Convex. Open flower, lower part: Flat.

*Petalage.*—On average 70 petals under normal conditions with 20 petaloids.

Color:

*Upon opening, petals.*—Outermost petals: Outer Side: Red group 55B to 55C with variegated streaking of Red Group 55D. Inner Side: Red Group 55B. Innermost petals: Outer Side: Red Group 55B. Inner Side: Red Group 55A to Red-Purple Group 58C.

*Upon opening, basal petal spots.*—Outermost petals: Outer Side: Yellow Group 4D. Inner Side: Yellow Group 4C. Innermost petals: Outer Side: Yellow Group 4C to 4D. Inner Side: Yellow Group 4B.

*After opening, petals.*—Outermost petals: Outer Side: Red Group 55B to 55C. Inner Side: Red Group 55B. Innermost petals: Outer Side: Red Group 55B. Inner Side: Red group 55A to Red-Purple Group 58C.

*After opening, basal petal spots.*—Outermost petals: Outer Side: Yellow Group 4D. Inner Side: Yellow Group 4C. Innermost petals: Outer Side: Yellow Group 4C to 4D. Inner Side: Yellow Group 4B.

General tonality: On open flower Red Group 55B. Changes in the general tonality at the end of the $7^{th}$ day Red Group 55B to 55C.

Petals:

*Petal reflex.*—Somewhat to strong.

*Petal margin.*—Entire.

*Shape.*—Pointed ovoid. Base: Acute to rounded. Apex: Round.

*Size.*—32 mm (10×26 mm (w).

*Thickness.*—Average.

*Arrangement.*—Not formal.

Petaloids:

*Shape.*—Elliptical and irregular. Base: Acute. Apex: Round.

*Color.*—Upper Surface: Red Group 55B to Red-Purple Group 58C. Lower Surface: Red Group 55B.

Reproductive organs:

*Pistils.*—Length: 3 mm. Quantity: 29 (actual count).

*Pollen.*—None.

*Anthers.*—Size: 3 mm. Color: Yellow Group 9A. Quantity: 60 (actual count).

*Filaments.*—Color: Yellow Group 9C. Length: 5 mm.

*Stigmas.*—Color: Yellow-Green Group 150D.

*Styles.*—Color: Yellow-Green Group 150C with intonations of Red-Purple Group 58B.

*Seed formation.*—Not observed.

PLANT

Plant growth: Vigorous, compact. When grown as a 12–15 cm pot plant, the average height of the plant itself is 22 cm and the average width is 13 cm.

Stems:

*Color.*—Young wood: Yellow-Green Group 144B. Older wood: Yellow-Green Group 144B.

*Length of stems.*—Average length 15 cm from flower to first branch.

*Surface texture.*—Young wood: Smooth. Older wood: Smooth.

*Internodal distance.*—2 mm.

Thorns: Incidence: None.

Plant foliage: Normal number of leaflets on normal leaves in middle of the stem: 5 leaflets.

*Compound leaf size.*—120 mm (l)×75 mm (w).

*Quantity.*—5 leaves per 10 cm of stem.

*Color.*—Juvenile foliage: Upper Leaf Surface: Yellow-Green Group 144A. Lower Leaf Surface: Yellow-Green Group 146B. Mature foliage: Upper Leaf Surface: Green Group 137A to 139A. Lower Leaf Surface: Yellow-Green Group 147B to 147C. Anthocyanin intonation: Location: On margins of juvenile leaves a Greyed-Orange Group 165A.

Plant leaves and leaflets:

*Stipules.*—Size: 8 mm. Margins: Finely serrated with medium stipitate glands. Color: Green Group 137B.

*Petiole.*—Length: 23 mm. Width: 1 mm. Color: Above: Green Group 137B. Underneath: Yellow-Green Group 144A with thorns and stipitate glands.

*Rachis.*—Length: 30 mm. Width: 1 mm. Above: Green Group 137B. Underneath: Yellow-Green Group 144A with thorns and stipitate glands.

*Leaflet.*—Size: 46 mm (l)×26 mm (w). Shape: Generally ovate. Apex is mucronate. Base is attenuate to rounded. Texture: Smooth. Arrangement: Odd pinnate. Venation: Reticulate. Leaf Gloss: Glossy.

Disease resistance: Average resistance to mildew, black spot, and Botrytis under normal glasshouse growing conditions in Fredensborg, Denmark.

It is claimed:

1. A new and distinct variety of rose plant of the miniature class, substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *

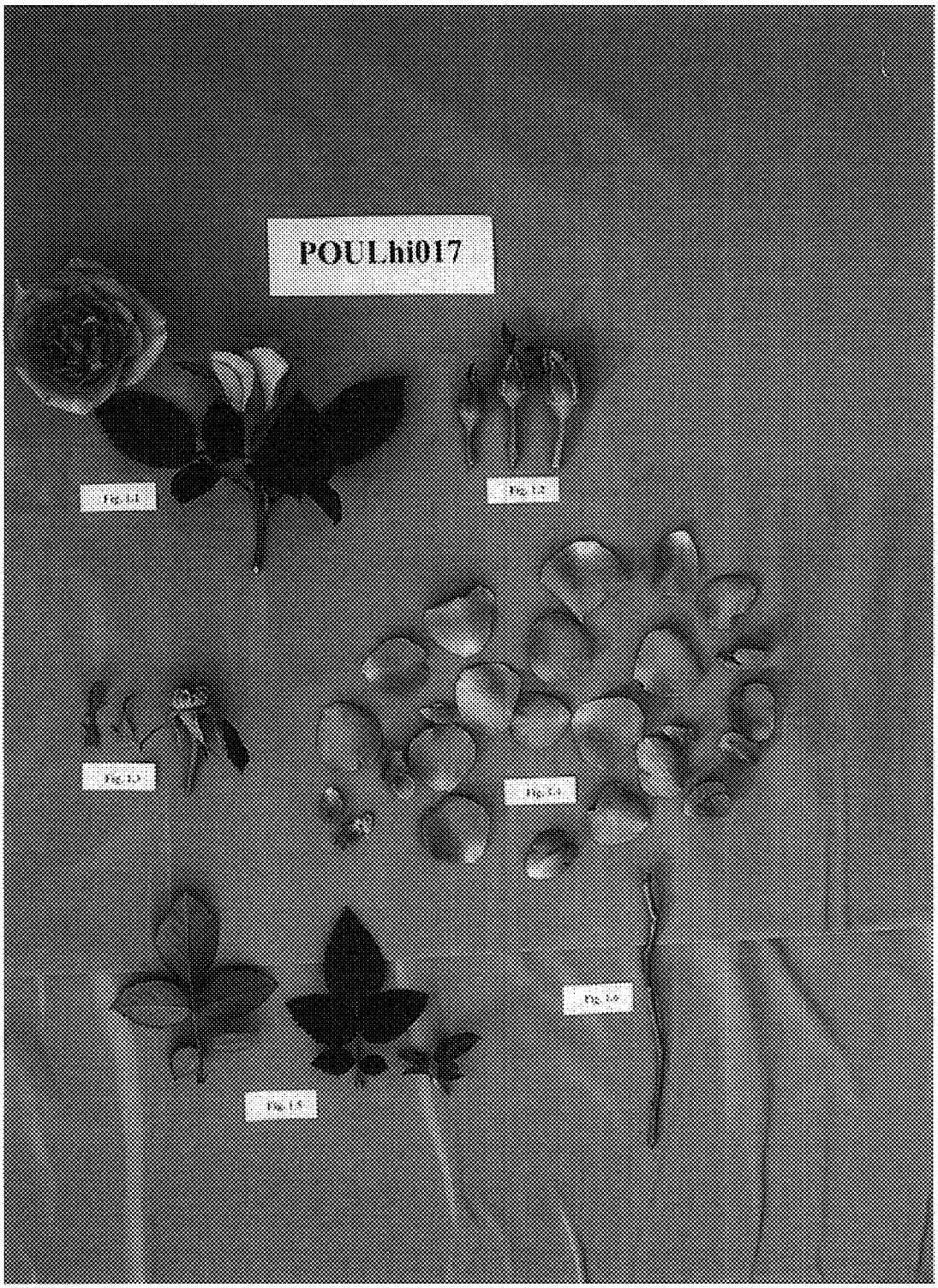
POULhi017